United States Patent [19]
Sackin et al.

[11] Patent Number: 5,738,863
[45] Date of Patent: Apr. 14, 1998

[54] HONEY BEE REPELLENT COMPOSITION COMPRISING TEA TREE OIL

[76] Inventors: Bradley M. Sackin, 3030 Brookdale Rd., Studio City, Calif. 91604; Yoram Fishman, 2375 Third St., Riverside, Calif. 92507

[21] Appl. No.: 779,650

[22] Filed: Jan. 15, 1997

Related U.S. Application Data

[63] Continuation of Ser. No. 226,694, Apr. 12, 1994, abandoned.

[51] Int. Cl.$^6$ ................................................ A01N 27/00
[52] U.S. Cl. .................. 424/405; 424/45; 424/195.1; 424/DIG. 10; 514/937; 514/944; 514/919
[58] Field of Search .................. 424/405, 45, 195.1, 424/DIG. 10, 43; 514/937, 944, 957, 919

[56] References Cited

U.S. PATENT DOCUMENTS

| | | | |
|---|---|---|---|
| 5,030,660 | 7/1991 | Norris et al. | 514/762 |
| 5,093,326 | 3/1992 | Herman | 514/172 |
| 5,109,022 | 4/1992 | Jeanne et al. | 514/552 |
| 5,208,029 | 5/1993 | Plummer et al. | 424/405 |
| 5,258,182 | 11/1993 | Delts | 424/195.1 |
| 5,258,408 | 11/1993 | Steltenkamp | 514/625 |

FOREIGN PATENT DOCUMENTS

| | | |
|---|---|---|
| 9307874 | 4/1993 | WIPO . |
| 17558 | 9/1993 | WIPO . |

OTHER PUBLICATIONS

Jacobs, M. R. et al. (1994). *Clinical Toxicology* 32(4): 461–464.

Brophy et al., Gas Chromatographic Quality Control for Oil of Melaleuca Terpinen–4–ol Type (Australian Tea Tree), 1989, *J. Agric. Food Chem*, vol. 37, No. 5.

Olsen, C. B. Australian Tea Tree Oil. Kali Press, Arizona, 1989.

*Primary Examiner*—Raj Bawa
*Attorney, Agent, or Firm*—Loeb & Loeb LLP

[57] ABSTRACT

A social stinging insect repellent composition comprises effective repelling amounts of tea tree oil and benzaldehyde, wherein said social stinging insect is a member of the order Hymenoptera and said tea tree is *melaleuca alternifolia*.

5 Claims, No Drawings

HONEY BEE REPELLENT COMPOSITION COMPRISING TEA TREE OIL

This is a continuation of application Ser. No. 08/226,694 filed on Apr. 12, 1994, now abandoned.

FIELD OF THE INVENTION

The present invention relates to an improved composition for repelling social stinging insects, such as bees, and more particularly to a repellent composition which is comprises tea tree oil and benzaldehyde.

BACKGROUND OF THE INVENTION

Control of insects, such as bees, can be effected either by the use of insecticides or by the use of non-insecticidal repellents. It is often desirable to use non-toxic, non-insecticidal repellents for environmental, health and economic reasons. An additional advantage of repellents is the fact that, since repellents do not kill the insects, populations of the target insects will not select as readily for resistance to the repellent. Non-toxic repellents are particularly desirable with respect to useful insects such as honey bees (*Apis mellifera*), in view of the beneficial functions, such as crop pollination, performed by these insects.

Various non-insecticidal repellent compositions are known. A widely-used, all-purpose insect repellent is N,N-diethyl-m-toluamide, or "DEET".

U.S. Pat. No. 5,258,408, to Steltenkamp, discloses the use of N-alkyl neoalkanamides as insect repellents. These compounds are particularly effective against mosquitoes and cockroaches.

U.S. Pat. No. 5,093,326, to Herman, teaches the use of ozonides of unsaturated hydrocarbons.

U.S. Pat. No. 5,109,022, to Jeanne et al., describes the use of compositions comprising at least one of methyl myristate, methyl palmitate and butyl palmitate to repel social stinging insects, such as bees and wasps. Such compounds occur naturally in the secretions of certain social wasps, which the wasps use to repel other insects such as ants.

Naturally occurring compounds are particularly desirable for use as insect repellents. For example, U.S. Pat. No. 5,030,660, to Norris et al., reveals the use of 1-dodecene, a volatile substance which occurs in certain plants.

The use of an extract prepared from the bark and leaves of the Wax-Myrtle (*Myrica cerifera*) to repel insects such as fleas and ticks from the coat of an animal is revealed in U.S. Pat. No. 5,258,182, to Delts.

An insect repellent effective against mosquitoes and other flying insects is prepared from a mixture of plant oils including Oil of *Hedeoma pulegioides*, Oil of *Pimpinella anisum* and Oil of Chrysanthemum, as taught by Plummer et al. in U.S. Pat. No. 5,208,029.

It would be desirable to provide an improved composition effective in repelling bees and other social stinging insects, preferably using naturally occurring ingredients which are non-toxic.

SUMMARY OF THE PREFERRED EMBODIMENTS

In accordance with one aspect of the present invention, there has been provided a social stinging insect repellent composition comprising effective repelling amounts of tea tree oil and benzaldehyde.

According to another aspect of the present invention, there has been provided a method of repelling social stinging insects comprising the step of exposing the insects to a composition comprising effective repelling amounts of tea tree oil and benzaldehyde. Preferably, the insects to be repelled are bees.

Other objects, features and advantages of the present invention will become apparent to those skilled in the art from the following detailed description. It is to be understood, however, that the detailed description and specific examples, while indicating preferred embodiments of the present invention, are given by way of illustration and not limitation. Many changes and modifications within the scope of the present invention may be made without departing from the spirit thereof, and the invention includes all such modifications.

DETAILED DESCRIPTION OF THE PREFERRED EMBODIMENTS

Tea tree oil is an essential oil of the tea tree, *Melaleuca alternifolia*, which is native to eastern Australia. It is non-toxic and non-irritating to the skin. Tea tree oil has long been known as being useful as, for example, a machine cutting oil, perfumery toner, flavoring and antiseptic agent, and antimicrobial agent. See, e.g., Brophy et al., J. Agric. Food Chem. 37:5, pp. 1330–35 (1989) (analysis of tea tree oil); Olsen, *Australian Tea Tree Oil* (Kali Press 1989).

Surprisingly, it has now been discovered that tea tree oil, in combination with benzaldehyde, can be used to prepare a highly effective, non-toxic repellent composition that is free of harsh chemicals, is environmentally friendly, can be applied topically to humans or animals, and discourages or deters social stinging insects from stinging humans and animals. By "social stinging insects" is meant in particular members of the order Hymenoptera, including bees, wasps and yellow jackets. The inventive composition is especially effective in repelling bees.

Both tea tree oil and benzaldehyde are present in the repellent formulation of the invention in amounts effective to repel social stinging insects, deterring them from stinging.

Preferably, the tea tree oil is present in the formulation in an amount from about 2.5% to 20% w/w, more preferably about 2.5% to 10% w/w. Tea tree oil can be obtained commercially, for example, from Melaleuca Estates of America.

Preferably, the benzaldehyde is present in the formulation in an amount from about 1.5% to 20% w/w, more preferably about 1.5% to 10% w/w. Benzaldehyde is readily available commercially, for example from Sigma Chemical (St. Louis, Mo.).

The inventive formulation can be prepared in any desired delivery form, for example, as a spray, cream, lotion, balm, oil or solid, such as a roll-on, for personal use, or a solid strip. For example, sprays can be prepared using conventional propellants, such as propane, butane, isobutane, either alone or in various mixtures known to those skilled in the art. Other conventional formulations, including known carriers and additives, will be readily apparent to those skilled in the art.

Typical liquid carriers useful in preparing repellent formulations according to the invention include water, alcohols such as methyl, ethyl, propyl and isopropyl alcohol, glycols, ketones, ethers, hydrocarbons, etc. Appropriate amounts of the liquid carrier can readily be determined by those skilled in the art. For example, when alcohols are used as liquid carriers, they can be present in amounts from about 5% to 80% w/w, in particular 10% to 60% w/w.

Exemplary additives useful in the inventive formulations include fragrances, antimicrobial agents, emulsifiers, pH adjusting agents, waxes, etc.

The formulations according to the invention can safely be applied to the skin of a human or animal, and can also be applied to clothing or any other porous or nonporous surfaces.

The following non-limiting examples illustrate formulations of repellent compositions according to the invention.

EXAMPLE 1

Aerosol spray

To SD alcohol 40 (200 proof) (78.00% w/w) are added tea tree oil (10.00w/w), benzaldehyde (10.00% w/w) and fragrance (2.00% w/w). The mixture is thoroughly mixed. An aerosol spray is then prepared from mixture (70.00% w/w) and propellant (30.00% w/w).

Exemplary propellants include the following:

a) For use on skin and sensitive areas: 85% isobutane, 15% propane. Pressure 45 psig at 70° C.

b) For use on clothing, furnishing and physical environments: 50% butane, 50% propane. Pressure 70 psig at 70° C.

EXAMPLE 2

Aerosol spray

To SD alcohol 40 (200 proof) (85.50% w/w) are added tea tree oil (2.50% w/w), benzaldehyde (10.00% w/w) and fragrance (2.00% w/w). The mixture is thoroughly mixed. An aerosol spray is then prepared from mixture (70.00% w/w) and propellent (30.00% w/w).

EXAMPLE 3

Pump spray

TO SD alcohol 40 (200 proof) (78.00% w/w) are added tea tree oil (10.00% w/w), benzaldehyde (10.00% w/w) and fragrance (2.00% w/w). The mixture is thoroughly mixed.

EXAMPLE 4

Skin cream (oil in water emulsion)

To deionized water (60.90% w/w) are added Carbomer 934 (0.40% w/w) with good mixing and heating to 75° C. Then propylene glycol (1.00% w/w) and methylparaben (0.20% w/w) are added to the mixture and dissolved.

In a separate container the following ingredients are mixed and dissolved with heating to 75° C. (amounts are in % w/w):

| | |
|---|---|
| PEG-8 C12–18 alkyl ester | 8.00 |
| Petrolatum | 4.00 |
| Acetylated lanolin | 1.00 |
| Propylparaben | 0.10 |
| Amphisol CA | 0.20 |
| Triethanolamine | 1.00 |

The resulting mixture is added to the water mixture and emulsified for 30 minutes. After cooling to 45° C., tea tree oil (10.00% w/w), benzaldehyde (10.00% w/w), Germall 115 (0.20% w/w), soluble collagen (1.00% w/w) and fragrance (2.00% w/w) are added with thorough mixing.

EXAMPLE 5

Skin cream (water in oil emulsion)

The following ingredients are combined and heated to 75° C. to melt and dissolve (amounts in % w/w):

| | |
|---|---|
| Mineral oil | 15.00 |
| Benzaledhyde | 10.00 |
| Tea tree oil | 10.00 |
| Paraffin wax | 7.00 |
| Beeswax | 8.00 |
| Arlacel 165 | 2.50 |
| Stearyl alcohol | 1.25 |
| Tocopherol | 0.10 |

The resulting mixture is thoroughly stirred until uniform.

In a separate container the following ingredients are heated to 75° C. to dissolve:

| | |
|---|---|
| Water, deionized | 42.95 |
| Sodium borate decahydrate | 0.50 |
| Methylparaben | 0.20 |

The two phases are then combined and emulsified for 30 minutes and cooled to 45° C. Then glydant (0.50% w/w) and fragrance (2.00% w/w) are added and the mixture is stirred until uniform.

EXAMPLE 6

Skin lotion

To deionized water (67.90% w/w) is added Carbomer 941 (0.10% w/w) with good mixing while heating to 75° C. Glycerin (4.00% w/w), triethanolamine (1.00% w/w) and methylparaben (0.20% w/w) are added and the solution is mixed until uniform.

Separately, the following ingredients are combined while heating to 75° C. (amounts in % w/w):

| | |
|---|---|
| Stearic acid | 2.50 |
| Acetylated lanolin | 1.30 |
| Cetyl alcohol | 0.50 |
| Propylparaben | 0.10 |
| Octyl dimethyl cinnamate | 0.10 |

When uniform, the mixture is added to the first mixture. The combined mixtures are emulsified for 30 minutes, then cooled with stirring to 55° C. Tea tree oil (10.00% w/w) and benzaldehyde (10.00% w/w) are added with thorough mixing. The mixture is then cooled to 45° C., at which point germall 115 (0.30% w/w) and fragrance (2.00% w/w) are added.

EXAMPLE 7

Roll-on applicator and/or dauber-type applicator

To deionized water (69.05% w/w) is added veegum (2.00% w/w) with thorough mixing. Methylparaben (0.20% w/w) and propylparaben (0.10% w/w) are added with heating to 75° C. Emulsifying wax NF (6.00% w/w) is then added with mixing until melted. Hydroxypropyl methylcellulose (0.50% w/w) is sifted into the mixture with rapid stirring until the mixture is uniform. The mixture in then cooled to 55° C.

Separately, tea tree oil (10.00% w/w), benzaldehyde (10.00% w/w), tincture of benzoin (0.50% w/w) and fragrance (1.50% w/w) are mixed and dissolved. The mixture is added to the first solution and mixed until uniform, then cooled to 40° C. Dowicill 115 (0.10% w/w) and citric acid (0.05% w/w) are added with thorough mixing, adjusting the pH of the mixture to 4.5.

EXAMPLE 8

Solid

Propylene glycol (65.00% w/w), sodium stearate (8.00% w/w) and water (5.00% w/w) are heated to 80° C. to dissolve to a clear solution. The mixture is then cooled to 50° C. Tea tree oil (10.00% w/w), benzaldehyde (10.00% w/w), and fragrance (2.00% w/w) are added with slow stirring until dissolved, then cooled.

EXAMPLE 9

Oil

The following ingredients are mixed to dissolve (amounts in % w/w):

| | |
|---|---|
| Mineral oil | 60.00 |
| Benzaldehyde | 10.00 |
| Tea tree oil | 10.00 |
| Isopropyl myristate | 10.00 |
| Cyclomethicone | 8.00 |
| Fragrance | 2.00 |

EXAMPLE 10

Experimental

The effectiveness of formulations according to the invention in repelling bees was tested as follows:

A) Patch test

Formulations according to the invention, and control formulations, were applied to a suede patch 2"×2", at a concentration of approximately 33 g/m$^3$. A 15% DEET solution was used for comparison. Two patches were then waived in front of a bee colony entrance, one treated, the other untreated, in random position left or right. The number of stings on the targets in 30 seconds was determined.

Each compound was tested 10 times. The mean number of stings are given in Table 1.

TABLE 1

| | Number of stings in suede | |
|---|---|---|
| | Treated | Untreated |
| DEET | 24.0 | 46.2 |
| Ex. 1 | 7.0 | 34.0 |
| Ex. 2 | 18.6 | 26.9 |
| Acetone control | 23.4 | 49.2 |

As shown, both of the inventive formulations significantly reduced the number of bee sting in the treated patch. The formulation of Example 1 was especially effective. The presence of the patches treated with the inventive formulations in proximity to the untreated patches also appear to have reduced the number of stings in the untreated patches, as shown by the comparison with the DEET and acetone untreated patches.

B) Spray test

Colonies of bees were deliberately disturbed to create a pool of defending workers. Experimenters gathered a large number of the defenders around themselves and moved to the testing area. Photographs were taken of the experimenter and the bees in the air to establish the initial (pre-test) number of bees. The experimenters then sprayed formulations according to the invention around themselves at the flying bees for about 10 seconds. Two photographs were taken at 5 and 10 seconds. Then a suede leather target was waved in front of the experimenter for 15 seconds, and the number of stings in the target were counted. Two more photographs of flying bees were made during target-waving, at 10 and 15 seconds. It was noted that bees often returned to some extent when the stimulus of the moving patch was present.

Each spray (including a control with no repellent ingredient) was tested in random order during one replicate, with each of three experimenters using every spray once. The test sequence was repeated six times in three different apiaries, on three separate days, for a total of 18 tests of each spray. Mean test results are given in Table 2.

TABLE 2

| | Number of stings | Number of bees initially | Number of bees in air after: | |
|---|---|---|---|---|
| | | | spray | patch |
| DEET | 40.1 | 135.6 | 93.9 | 85.9 |
| Ex. 1 | 44.0 | 133.8 | 98.3 | 108.5 |
| Ex. 2 | 48.4 | 146.2 | 129.1 | 121.3 |
| (nothing) | 45.1 | 133.2 | 138.8 | 132.8 |

As shown, the inventive formulations, more particularly the formulation of Example 1, were effective in repelling bees from the vicinity of the experimenter.

What is claimed is:

1. A social stinging Insect repellent composition comprising about 2.5 to 20% tea tree oil, about 1.5 to 20% benzaldehyde, and 5 to 80% of an alcohol, based on the total weight of the composition, wherein said social stinging insect is a honey bee.

2. The composition of claim 1, wherein said tea tree oil is about 2.5% to 10% of the total weight of the composition.

3. The composition of claim 2, wherein said benzaldehyde is about 1.5% to 10% of the total weight of the composition.

4. The composition of claim 1 in the form of a spray, a cream, a lotion, an oil or a solid.

5. The composition of claim 1, wherein said alcohol is selected from the group consisting of methyl, ethyl, propyl and isopropyl alcohol.

* * * * *